(12) United States Patent
Aoki et al.

(10) Patent No.: US 10,913,731 B2
(45) Date of Patent: Feb. 9, 2021

(54) EPOXY-OXETANE COMPOUND, METHOD FOR SYNTHESIZING SAME, AND USE OF SAID COMPOUND

(71) Applicant: SHIKOKU CHEMICALS CORPORATION, Kagawa (JP)

(72) Inventors: Kazunori Aoki, Kagawa (JP); Naoto Okumura, Kagawa (JP); Takashi Kashiwabara, Kagawa (JP); Yusuke Araki, Kagawa (JP); Akihito Otsuka, Kagawa (JP); Takeshi Kumano, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 0 days.

(21) Appl. No.: 16/756,576

(22) PCT Filed: Oct. 15, 2018

(86) PCT No.: PCT/JP2018/038383
§ 371 (c)(1),
(2) Date: Apr. 16, 2020

(87) PCT Pub. No.: WO2019/082717
PCT Pub. Date: May 2, 2019

(65) Prior Publication Data
US 2020/0270236 A1  Aug. 27, 2020

(30) Foreign Application Priority Data

Oct. 23, 2017  (JP) ................................. 2017-204824
Sep. 20, 2018  (JP) ................................. 2018-175778

(51) Int. Cl.
*C07D 407/14* (2006.01)
*C08G 59/24* (2006.01)
*C08G 65/18* (2006.01)

(52) U.S. Cl.
CPC .......... *C07D 407/14* (2013.01); *C08G 59/24* (2013.01); *C08G 65/18* (2013.01)

(58) Field of Classification Search
None
See application file for complete search history.

(56) References Cited

U.S. PATENT DOCUMENTS

| 3,205,207 A | 9/1965 | Vandenberg et al. |
| 3,457,193 A | 7/1969 | Tinsley et al. |
| 5,362,848 A | 11/1994 | Archibald et al. |

| 2013/0331476 A1 | 12/2013 | Bae et al. |
| 2015/0093585 A1 | 4/2015 | Bae et al. |
| 2017/0145253 A1 | 5/2017 | Bae et al. |
| 2017/0260150 A1 | 9/2017 | Nose et al. |
| 2018/0215949 A1 | 8/2018 | Bae et al. |

FOREIGN PATENT DOCUMENTS

| CN | 102659720 | 9/2012 | |
| JP | 2005-2191 | 1/2005 | |
| JP | 2007-270070 | 10/2007 | |
| JP | 2009-138116 | 6/2009 | |
| JP | 2010-111713 | 5/2010 | |
| JP | 2011-208089 | 10/2011 | |
| JP | 2013-139527 | 7/2013 | |
| JP | 2013-151443 | 8/2013 | |
| JP | 2015-524855 | 8/2015 | |
| WO | WO-2011043474 A1 * | 4/2011 | ............ C08L 63/00 |
| WO | 2016/088749 | 6/2016 | |

OTHER PUBLICATIONS

International Search Report, dated Dec. 4, 2018 in corresponding International Patent Application No. PCT/JP2018/038383, with English language translation.
Registry (STN), Jan. 16, 2018, RN: 2170360-32-2.

* cited by examiner

*Primary Examiner* — Zinna Northington Davis
(74) *Attorney, Agent, or Firm* — Wenderoth, Lind & Ponack, L.L.P.

(57) ABSTRACT

The purpose of the present invention is to provide: a novel curable compound which can be expected to be used as a raw material for photocurable resins and thermosetting resins; a method for synthesizing said compound; a resin composition containing said compound; and a cured product thereof. This compound is an epoxy-oxetane compound represented by a formula, and this compound has a structure in which two epoxycyclohexyl groups (groups in which an oxirane ring and a cyclohexane ring are condensed) are bonded to an oxetane ring via a connector having one ether bond. In formula (I'), $R_1$ to $R_3$ may be the same as, or different from, each other, and each denote a hydrogen atom or a methyl group. n is 1 or 2.

[Chem. 1]

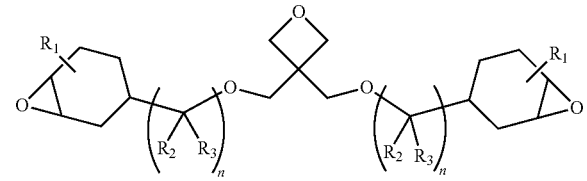

(I')

4 Claims, 1 Drawing Sheet

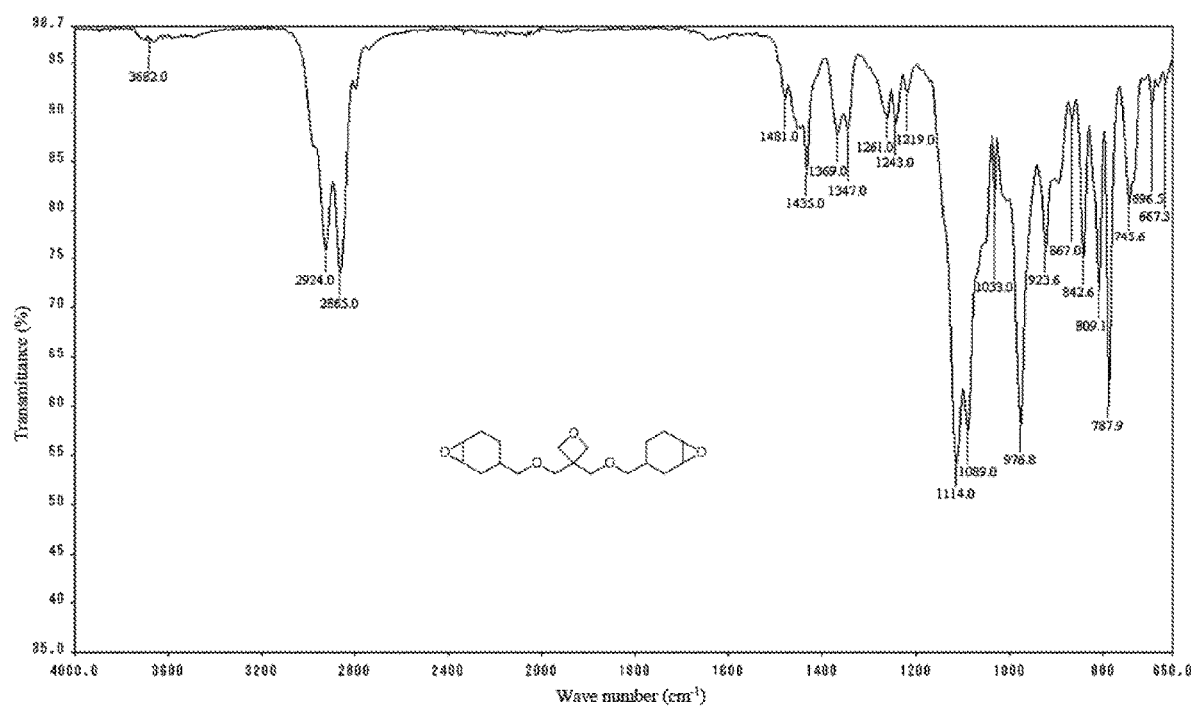

EPOXY-OXETANE COMPOUND, METHOD FOR SYNTHESIZING SAME, AND USE OF SAID COMPOUND

TECHNICAL FIELD

The present invention relates to a novel epoxy-oxetane compound, a method for synthesizing the compound, a resin composition containing the compound, and a cured product thereof.

BACKGROUND ART

Oxetane compounds have recently attracted attention as a photo-curable and thermal-curable monomer, and a resin composition containing an oxetane compound as a component has small shrinkage during curing, and a cured product (resin) thereof is excellent in toughness, mechanical properties, heat resistance, electrical properties, water resistance, weather resistance, transparency, and the like.

Because of these excellent characteristics, the resin composition containing an oxetane compound has been used as a raw material for coating materials, paints, inks, bonding materials, adhesive materials, films, pastes, optical materials, sealing materials, resist materials, or the like.

Conventional techniques related to the present invention are described below with reference to literatures.

The invention described in Patent Literature 1 relates to an epoxyoxacyclobutane compound and a polymer thereof.

This literature describes, as an example of the epoxyoxacyclobutane compound, 3,3-di(2,3-epoxypropoxymethyl)oxacyclobutane and a methyl substitution product thereof, that is, 3,3-di(2,3-epoxy-2-methylpropoxymethyl)oxacyclobutane (See chemical formula Ref-1).

[Chem. 1]

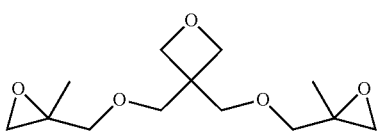

(Ref-1)

The invention described in Patent Literature 2 relates to an active energy ray-curable inkjet ink and a printed product.

This literature describes compounds represented by chemical formulas Ref-2 to Ref-4 as examples of a non-acrylic cationic polymerizable compound having an oxirane ring (epoxy group) and an oxetane ring in the same molecule.

[Chem. 2]

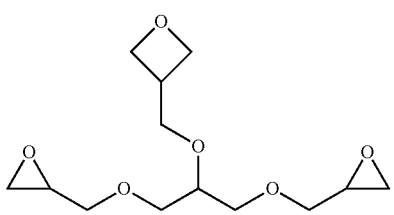

(Ref-2)

[Chem. 3]

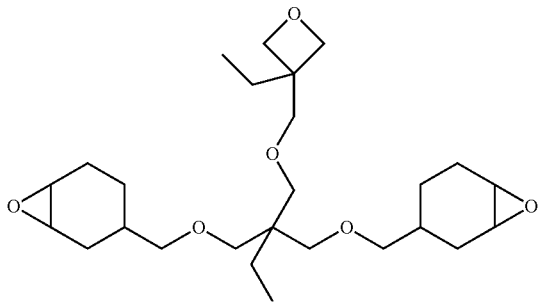

(Ref-3)

[Chem. 4]

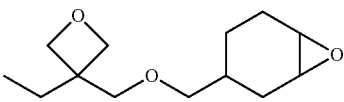

(Ref-4)

Patent Literatures 3 to 5 also describe compounds represented by the above-mentioned chemical formulas Ref-'2 to Ref-4 or analogous compounds thereof.

CITATION LIST

Patent Literature

Patent Literature 1: U.S. Pat. No. 3,457,193 specification
Patent Literature 2: JP-A-2005-002191
Patent Literature 3: JP-A-2007-270070
Patent Literature 4: JP-A-2010-111713
Patent Literature 5: JP-A-2011-208089

SUMMARY OF INVENTION

Technical Problem

An object of the present invention is to provide a curable compound suitable as a raw material for a photo-curable resin and a thermosetting resin, and a method for synthesizing the compound. Another object is to provide a resin composition containing the compound and a cured product thereof.

Solution to Problem

The present inventors have found that the intended object can be achieved by employing, as the curable compound, a compound having a certain structure in which two epoxycyclohexyl groups are connected to an oxetane ring via a spacer, and thus they have completed the present invention.

That is, a first invention relates to an epoxy-oxetane compound represented by the chemical formula (I).

[Chem. 5]

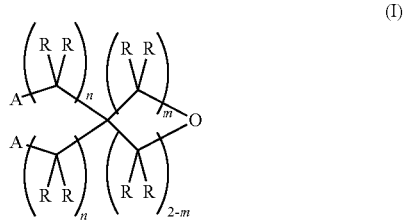

(I)

(In the formula (I), A's may be the same as or different from each other, and each independently represents a group represented by the chemical formula (II). R's may be the same as or different from each other, and each independently represents a hydrogen atom or a hydrocarbon group having a carbon number of 1 to 20. m represents an integer of 0 to 2. n's may be the same as or different from each other, and each independently represents an integer of 0 to 20.)

[Chem. 6]

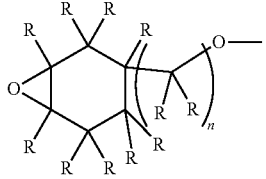

(II)

(In the formula (II), R's may be the same as or different from each other, and each independently represents as hydrogen atom or a hydrocarbon group having a carbon number of 1 to 20. n represents an integer of 0 to 20.)

A second invention relates to a method for synthesizing the epoxy-oxetane compound of the first invention, including reacting an oxetane compound represented by the chemical formula (III) and an olefin compound represented by the chemical formula (IV) to generate an olefin-oxetane compound represented by the chemical formula (Ia) having a double bond, and then epoxidizing the double bond.

[Chem. 7]

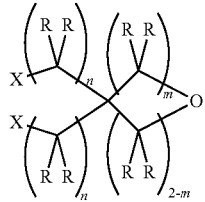

(III)

(In the formula (III), R's may be the same as or different from each other, and each independently represents a hydrogen atom or a hydrocarbon group having a carbon number of 1 to 20. m represents an integer of 0 to 2. n's may be the same as or different from each other, and each independently represents an integer of 0 to 20. X's may be the same as or different from each other, and each independently represents a fluorine atom, a chlorine atom, a bromine atom, au iodine atom, a mesyl group (OMs), a tosyl group (OTs), or a trifluoromethyl group (OTf).)

[Chem. 8]

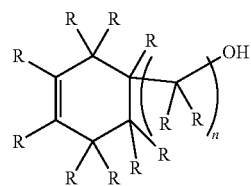

(IV)

(In the formula (IV), R's may be the same as or different from each other, and each independently represents a hydrogen atom or a hydrocarbon group having a carbon number of 1 to 20. n represents an integer of 0 to 20.)

[Chem. 9]

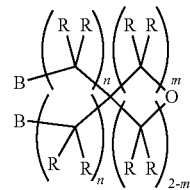

(Ia)

(In the formula (Ia), B's may be the same as or different from each other, and each independently represents a group represented by the chemical formula (V). R's may be the same as or different from each other, and each independently represent a hydrogen atom or a hydrocarbon group having a carbon number of 1 to 20. m represents an integer of 0 to 2. n's may be the same or different from each other, and each independently represents an integer of 0 to 20.)

[Chem. 10]

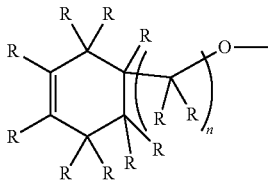

(V)

(In the formula (V), R and n have the same meanings as those in the chemical formula (IV).)

A third invention relates to a resin composition containing the epoxy-oxetane compound of the first invention.

A fourth invention relates to a cured product obtained by curing the resin composition of the third invention.

Advantageous Effects of Invention

In the case where the epoxy-oxetane compound of the present invention is used as a raw material (curable compound) of a photo-curable resin and a thermosetting resin, a resin composition exhibiting a crosslinking function and having excellent curability (high curing speed) can be obtained. In addition, the cured product of the resin composition of the present invention has excellent heat resistance and dimensional stability, and is superior in brittleness as compared with a cured product of a conventional resin composition exhibiting high heat resistance.

BRIEF DESCRIPTION OF DRAWINGS

FIG. 1 is an IR spectrum chart of a colorless transparent liquid obtained in Example 1.

DESCRIPTION OF EMBODIMENTS

The epoxy-oxetane compound of the present invention has a structure in which two epoxycyclohexyl groups (an oxirane ring and a cyclohexane ring are condensed) are each bonded to an oxetane ring via a spacer having one ether bond, as shown in the chemical formula (I).

[Chem. 11]

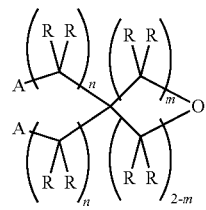

(I)

(In the formula (I), A's may be the same as or different from each other, and each independently represents a group represented by the chemical formula (II). R's may be the same as or different from each other, and each independently represents a hydrogen atom or a hydrocarbon group having a carbon number of 1 to 20. m represents an integer of 0 to 2. n's may be the same as or different from each other, and each independently represents an integer of 0 to 20.)

[Chem. 12]

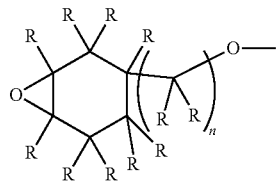

(II)

(In the formula (II), R's may be the same as or different from each other, and each independently represents a hydrogen atom or a hydrocarbon group having a carbon number of 1 to 20. n represents an integer of 0 to 20.)

The epoxy-oxetane compound represented by the chemical formula (I), of the present invention is preferably an epoxy-oxetane compound represented by the chemical formula (I') from the viewpoints of easy availability of raw materials and simplification of the synthesis process.

[Chem. 13]

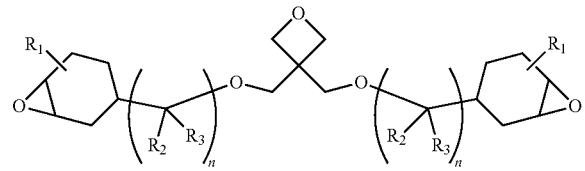

(I')

(In the formula (I'), $R_1$ to $R_3$ are the same as or different from each other, and each represents a hydrogen atom or a methyl group. n represents 1 or 2.)

Preferred examples of such an epoxy-oxetane compound include epoxy-oxetane compounds represented by chemical formulas (I-1) to (1-9).

[Chem. 14]

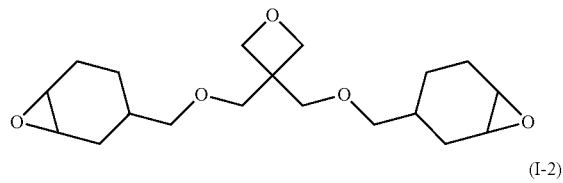
(I-1)

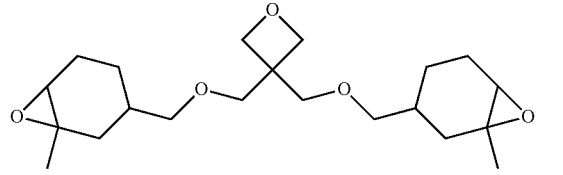
(I-2)

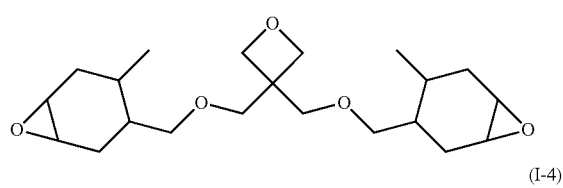
(I-3)

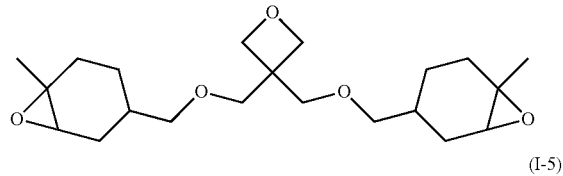
(I-4)

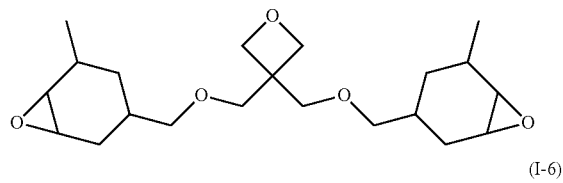
(I-5)

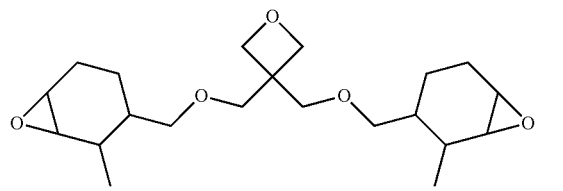
(I-6)

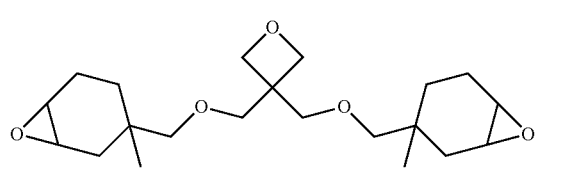
(I-7)

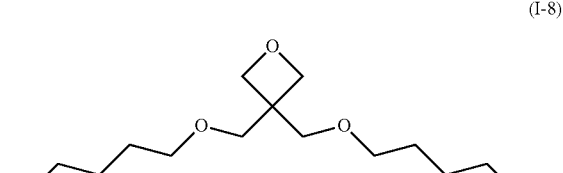
(I-8)

(I-9)

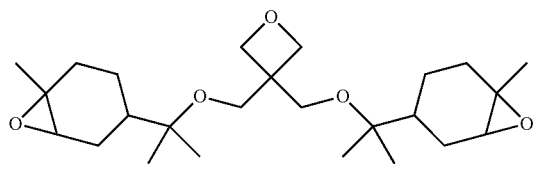

Method for Synthesizing Epoxy-oxetane Compound of the Present Invention

As described in the second invention, the epoxy-oxetane compound represented by the chemical formula (I) in the present invention can be synthesized by reacting an oxetane compound represented by the chemical formula (III) having a leaving group and an olefin compound represented by the chemical formula (IV) having a hydroxy group to generate an olefin-oxetane compound represented by the chemical formula (Ia), and then epoxidizing a double bond of this compound.

[Chem. 15]

(III)

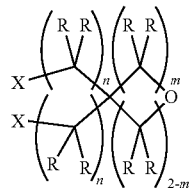

(In the formula (III), R's may be the same as or different from each other, and each independently represents a hydrogen atom or a hydrocarbon group having a carbon number of 1 to 20. m represents an integer of 0 to 2. n's may be the same as or different from each other, and each independently represents an integer of 0 to 20. X's may be the same as or different from each other, and each independently represents a fluorine atom, a chlorine atom, a bromine atom, an iodine atom, a mesyl group (OMs), a tosyl group (OTs), or a trifluoromethyl group (OTf).)

[Chem. 16]

(IV)

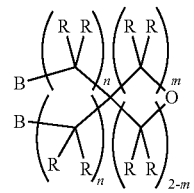

(In the formula (IV), R's may be the same as or different from each other, and each independently represents a hydrogen atom or a hydrocarbon group having a carbon number of 1 to 20. n represents an integer of 0 to 20.)

[Chem. 17]

(Ia)

(In the formula (Ia), B's may be the same as or different from each other, and each independently represents a group represented by the chemical formula (V). R's may be the same as or different from each other, and each independently represents a hydrogen atom or a hydrocarbon group having a carbon number of 1 to 20. m represents an integer of 0 to 2. n's may be the same as or different from each other, and each independently represents an integer of 0 to 20.)

[Chem. 18]

(V)

(In the formula (V), R and n have the same meanings as those in the chemical formula (IV).)

Similar to the case where the epoxy-oxetane compound represented by the chemical formula (I') is a preferred invention, from the viewpoints of easy availability of raw materials and simplification of the synthesis process, in the second invention, the epoxy-oxetane compound represented by the chemical formula (I') is preferably synthesized by reacting an oxetane compound represented by the Chemical formula (III') having a leaving group and an olefin compound represented by the chemical formula (IV') having a hydroxy group to generate an olefin-oxetane compound represented by the chemical formula (Ia'), and then epoxidizing a double bond of this compound (see reaction scheme (A)).

[Chem. 19]

Reaction scheme (A)

-continued

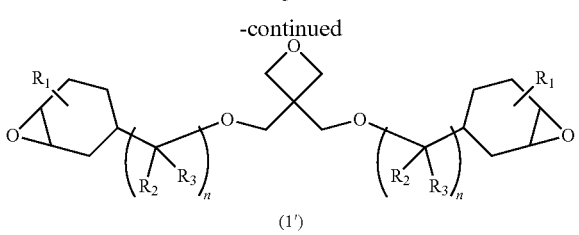

(1')

(In the formulas in the reaction scheme (A), $R_1$ to $R_3$ are the same as or different from each other, and each represents a hydrogen atom or a methyl group. n represents 1 or 2. X's may be the same as or different from each other, and each independently represents a fluorine atom, a chlorine atom, a bromine atom, an iodine atom, a mesyl group (OMs), a tosyl group (OTs), or a trifluoromethyl group (OTf).)

The olefin-oxetane compound represented by the chemical formula (Ia) (or (Ia')) can be synthesized in the presence of a base (i), and a catalyst (ii) for accelerating the reaction may be used. In addition, a reaction solvent (iii) may be used as long as the reaction is not inhibited.

In the reaction of epoxidizing the double bond of the olefin-oxetane compound, a general epoxidation (oxidation) method can be used. Examples of the method include a method using a peracid, a method using hydrogen peroxide with sodium tungstate as a catalyst, a method using hydrogen peroxide in combination with a base in an acetonitrile-alcohol solvent, and the like.

Examples of the oxetane compound having a leaving group (chemical formula (III)/(III')) include 3,3-bis(chloromethyl)oxetane, 3,3-bis(bromomethyl)oxetane, 3,3-bis(chloroethyl)oxetane, 3,3-bis(bromoethyl)oxetane, 3,3-bis(chloropapyl)oxetane, 3,3-bis(bromopropyl)oxetane, and the like, and 3,3-bis(bromomethyl)oxetane is preferred.

Examples of the olefin compound having a hydroxy group (chemical formula (IV)/(IV')) include 3-cyclohexene-1-methanol, 1-methyl-3-cyclohexene-1-methanol, 2-methyl-3-cyclohexene-1-methanol, 3-methyl-3-cyclohexene-1-methanol, 4-methyl-3-cyclohexene-1-methanol, 5-methyl-1-cyclohexene-1-methanol, 6-methyl-3-cyclohexene-1-methanol, 3-cyclohexene-1-ethanol, α-terpineol, and the like, and 3-cyclohexene-1-methanol is preferred.

The amount used (the amount charged) of the olefin compound is preferably in an appropriate molar ratio in the range of from 2 to 20 times with respect to the amount used (the amount charged) of the oxetane compound having a leaving group.

Examples of the base (i) include hydrides, hydroxides, carbonates, hydrogencarbonates and alkoxides of alkali metals or alkaline earth metals, organic amine compounds, and the like.

Specific examples thereof include sodium hydride, potassium hydride, sodium hydroxide, potassium hydroxide, sodium carbonate, potassium carbonate, sodium alkoxide, potassium alkoxide, triethylamine, and the like.

The amount used (the amount charged) of the base is preferably in an appropriate molar ratio in the range of, generally, from 2 to 20 times with respect to the amount used (the amount charged) of the oxetane compound having a leaving group.

Examples of the catalyst (ii) include quaternary ammonium salts, quaternary phosphonium salts and the like.

Examples of the quaternary ammonium salt include salts such as halides (fluorides, chlorides, bromides, and iodides) of tetrabutyl ammonium, tetramethyl ammonium, tetraethyl ammonium, tetrapropyl ammonium, tetrahexyl ammonium, tetraoctyl ammonium, tetradecyl ammonium, hexadecyltriethyl ammonium, dodecyltrimethyl ammonium, trioctylmethyl ammonium, octyltriethyl ammonium, benzyltrimethyl ammonium, benzitriethyl ammonium, benzyltributyl ammonium, benzyldimethyloctadecyl ammonium, and phenyltrimethyl ammonium.

Examples of the quaternary phosphonium salt include salts such as halides (fluorides, chlorides, bromides, and iodides) of tetrabutyl phosphonium, tetramethyl phosphonium, tetraethyl phosphonium, tetrapropyl phosphonium, tetrahexyl phosphonium, tetradecyl phosphonium, tetraoctyl phosphonium, triethyloctadecyl phosphonimn, trioctylethyl phosphonium, hexadecyltriethyl phosphonium tetraphenyl phosphonium, and methyltriphenyl phosphonium.

These substances may be used in combination as the catalyst (ii).

The amount used (the amount charged) of the catalyst (ii) is preferably in an appropriate molar ratio in the range of from 0.0001 to 1.0 time with respect to the amount used (the amount charged) of the oxetane compound having a leaving group.

The reaction solvent (iii) is not particularly limited as long as the reaction is not inhibited, and examples thereof include solvents such as water, methanol, ethanol, propanol, butanol, ethylene glycol, propylene glycol monomethyl ether, tetrahydrofuran, diethyl ether, dioxane, dimethoxyethane, polyethylene glycol (PEG-400), ethyl acetate, propyl acetate, butyl acetate, acetonitrile, benzene, toluene, xylene, dichloromethane, chloroform, carbon tetrachloride, dimethylformamide (DMF), dimethylacetamide (DMA), dimethyl sulfoxide (DMSO), and hexamethylphosphoramide (HMPA). One kind or two or more kinds in combination, selected from these, can be used in an appropriate amount.

The reaction temperature when synthesizing the olefin-oxetane compound represented by the chemical formula (Ia) (or (Ia')) is preferably set in the range of from 0 to 150° C., and more preferably set in the range of from 20 to 120° C. The reaction time is appropriately set depending on the set reaction temperature, and is preferably set in the range of from 1 to 48 hours.

After completion of the reaction, the olefin-oxetane compound, which is a precursor of a target substance, can be separated and taken out from the obtained reaction solution by, for example, a solvent extraction method.

Furthermore, if necessary, purification can be performed by utilizing means of washing with water or the like, activated carbon treatment, silica gel chromatogaphy, or the like.

In the above-mentioned reaction of epoxidizing the olefin-oxetane compound by using a peracid, peracids such as an came reagent, peracetic acid, and metachloroperbenzoic acid can be used. The amount used (the amount charged) of the peracid is preferably in an appropriate molar ratio in the range of from 1.0 to 5.0 times with respect to the double bond of the olefin-oxetane compound.

In the epoxidation reaction, the reaction solvent is not particularly limited as long as the reaction is not hindered, and examples thereof include: water; alcohols such as methanol, ethanol and 2-propanol; aliphatic hydrocarbons such as hexane and heptane; ketones such as acetone and 2-butanone; esters such as ethyl acetate and butyl acetate; aromatic hydrocarbons such as benzene, toluene and xylene; halogenated hydrocarbons such as methylene chloride, chloroform, carbon tetrachloride, chlorotrifluoromethane, dichloroethane, chlorobenzene, and dichlorobenzene; ethers such as diethyl ether, diisopropyl ether, tetrahydrofuran, dioxane, dimethoxyethane, and diethylene glycol dimethyl ether; amides such as formamide, dimethylformamide (DMF), dimethylacetamide (DMA), N-methyl-2-pyrrolidone, N-methylpyrrolidinone, and hexamethylphosphorotriamide; sulfoxides such as dimethyl sulfoxide (DMSO); and the like. These reaction solvents can be used alone or in combination of two or more thereof, in an appropriate amount.

The reaction temperature in this epoxidation reaction is generally in the range of from −10 to 150° C., and preferably in the range of from 0 to 100° C. The reaction time is appropriately set depending on the reaction temperature, and is generally set in the range of from 1 to 24 hours, and preferably in the range of from 1 to 6 hours.

After completion of the reaction, the epoxy-oxetane compound of the present invention, which is a target substance, can be separated and taken out from the obtained reaction solution by, for example, a solvent extraction method.

Furthermore, if necessary, purification can be performed by utilizing means of washing with water or the like, activated carbon treatment, silica gel chromatography, or the like.

In the above-described reaction of epoxidizing the olefin-oxetane compound by using hydrogen peroxide with sodium tungstate as a catalyst, hydrogen peroxide is used in a molar ratio of from 1.0 to 5.0 times with respect to the double bond of the olefin-oxetane compound. In addition, the amount used of the sodium tungstate is preferably in an appropriate molar ratio in the range of from 0.001 to 0.5 time with respect to the double bond of the olefin-oxetane compound.

In this epoxidation reaction, though it is not particularly limited as long as the reaction is not hindered, a reaction solvent same as in the above-described epoxidation using a peracid can be used for example.

Similar to the case of the above-described epoxidation using a peracid, the reaction temperature in this epoxidation reaction is generally set in the range of from −10 to 150° C., and preferably in the range of from 0 to 100° C. The reaction time is appropriately set depending on the reaction temperature, and is generally set in the range of from 1 to 24 hours, and preferably in the range of from 1 to 6 hours.

After completion of the reaction, similar to the case of the above-described epoxidation using a peracid, the epoxy-oxetane compound of the present invention can be separated and taken out from the obtained reaction solution by, for example, a solvent extraction method. In addition, purification may be performed if necessary.

In the above-described reaction of epoxidizing the olefin-oxetane compound by using hydrogen peroxide in an acetonitrile-alcohol solvent, the amount used of the hydrogen peroxide is preferably an appropriate molar ratio in the range of from 1.0 to 5.0 times of the double bond of the olefin-oxetane compound.

In addition, the amount used of the acetonitrile is preferably in an appropriate molar ratio in the range of from 0.5 to 5.0 times with respect to the olefin-oxetane compound.

The amount used of the alcohol is preferably an appropriate ratio in the range of from 10 to 80 wt % before the addition of hydrogen peroxide. It is preferable to set the pH within the range of 7 to 13 by using a base.

The alcohol used in this epoxidation is preferably a saturated alcohol having a carbon number of 1 to 4, and examples thereof include methanol, ethanol, n-propanol, 2-propanol, n-butanol, sec-butanol (2-butanol), and isobutanol (2-methyl-1-propanol). These alcohols can be used alone or in combination of two or more thereof, in an appropriate amount.

Examples of the base used in this epoxidation include hydroxides, carbonates or hydrogen carbonates of alkali metals or alkaline earth metals, or organic amine compounds. It is preferable to use sodium hydroxide, potassium hydroxide, potassium carbonate, and potassium hydrogen carbonate. These bases can be used alone or in combination of two or more thereof, in an appropriate amount.

Similar to the case of the above-described epoxidation using a peracid, the reaction temperature in this epoxidation reaction is generally set in the range of from −10 to 150° C., and preferably in the range of from 0 to 100° C. The reaction time is appropriately set depending on the reaction temperature, and is generally set in the range of from 1 to 48 hours, and preferably in the range of from 1 to 6 hours.

After completion of the reaction, similar to the case of the above-described epoxidation using a peracid, the epoxy-oxetane compound of the present invention can be separated and taken out from the obtained reaction solution by, for example, a solvent extraction method. In addition, purification may be performed if necessary.

Resin Composition of the Present Invention

The epoxy-oxetane compound of the present invention exhibits excellent curing performance.

That is, the resin composition containing the epoxy-oxetane compound (hereinafter, also referred to as a first curable compound in some cases) of the present invention can provide, by being cured, a cured product (resin) expected to exhibit excellent properties.

In the resin composition of the present invention, the first curable compound and another curable compound (hereinafter, also referred to as a second curable compound in some cases) other than the first curable compound can be used in combination.

In the case where the second curable compound coexists in addition to the first curable compound at the time when curing (polymerizing) the resin composition of the present invention, a cured product obtained by copolymerizing the first curable compound and the second curable compound can be obtained.

The second curable compound includes both a polymerizable monomer and a polymerizable oligomer (semi-cured product) having a structure in which the polymerizable monomers are polymerized.

Examples of the polymerizable monomer include known epoxy compounds (note: also referred to as epoxy resin in some cases), known oxetane compounds, known epoxy-oxetane compounds (having an oxirane ring and an oxetane ring in the molecule), known acrylic compounds (also referred to as acrylic resin in some cases), and the like.

Any epoxy compound can be used without particular limitation as long as it has an oxirane ring (epoxy group/glycidyl group) in the molecule, and examples thereof include:

polyglycidyl ethers obtained by reacting polyhydric phenols such as bisphenol A, bisphenol F, bisphenol AD, catechol, and resorcinol, or polyhydric alcohols such as glycerin and polyethylene glycol, with epichlorohydrin;

glycidyl ether esters obtained by reacting hydroxycarboxylic acids such as p-hydroxybenzoic acid and β-hydroxynaphthoic acid with epichlorohydrin;

polyglycidyl esters obtained by reacting polycarboxylic acids such as phthalic acid and terephthalic acid with epichlorohydrin;

glycidyl glycoluril compounds having two or more epoxy groups in the molecule, such as 1,3,4,6-tetraglycidylglycoluril;

alicyclic epoxy compounds such as 3',4'-epoxycyclohexylmethyl 3,4-epoxycyclohexanecarboxylate;

nitrogen-containing cyclic epoxy compounds such as triglycidyl isocyanurate and hydantoin epoxy compounds;

epoxidized phenol novolak resins: epoxidized cresol novolak resins; epoxidized polyolefins: cycloaliphatic epoxy resins; urethane-modified epoxy resins; as well as epoxy-modified organopolysiloxane compounds obtained by a hydrosilylation addition reaction of an organic compound having a carbon-carbon double bond and a glycidyl group with a silicon compound having a SiH group (e.g., epoxy-modified organopolysiloxane compounds disclosed in JP-A-2004-99751 and JP-A-2006-282988); and the like. These can be used in combination.

Any oxetane compound can be used without particular limitation as long as it has an oxetane ring (oxetanyl group/oxetane group) in the molecule, and examples thereof include:
3-ethyl-3-hydroxymethyl oxetane,
3-(meth)allyloxymethyl-3-ethyloxetane,
(3-ethyl-3-oxetanylmethoxy)methyl benzene,
4-fluoro-[1-(3-ethyl-3-oxetanylmethoxy)methyl]benzene,
4-methoxy-[1-(3-ethyl-3-oxetanylmethoxy)methyl]benzene,
[1-(3-ethyl-3-oxetanylmethoxy)ethyl]phenyl ether,
isobutoxymethyl (3-ethyl-3-oxetanylmethyl)ether,
isobornyloxyethyl (3-ethyl-3-oxetanylmethyl)ether,
isobornyl (3-ethyl-3-oxetanylmethyl)ether,
2-ethylhexyl (3-ethyl-3-oxetanylmethyl)ether,
ethyl diethylene glycol (3-ethyl-3-oxetanylmethyl)ether,
dicyclopentadien (3-ethyl-3-oxetanylmethyl)ether,
dicyclopentenyloxyethyl (3-ethyl-3-oxetanylmethyl)ether,
dicyclopentenyl (3-ethyl-3-oxetanylmethyl)ether,
tetrahydrofurfuryl (3-ethyl-3-oxetanylmethyl)ether,
2-hydroxyethyl (3-ethyl-3-oxetanylmethyl)ether,
2-hydroxypropyl (3-ethyl-3-oxetanylmethyl)ether,
butoxyethyl (3-ethyl-3-oxetanylmethyl)ether,
bornyl (3-ethyl-3-oxetanylmethyl)ether,
3,7-bis(3-oxetanyl)-5-oxa-nonane,
3,3'-[1,3-2-methylenyl)propanediylbis(oxymethylene)]bis-(3-ethyloxetane),
1,4-bis[(3-ethyl-3-oxetanylmethoxy)methyl]benzene,
1,2-bis[(3-ethyl-3-oxetanylmethoxy)methyl]ethane,
1,3-bis[(3-ethyl-3-oxetanylmethoxy)methyl]propane,
ethylene glycol bis(3-ethyl-3-oxetanylmethyl)ether,
dicyclopentenyl bis(3-ethyl-3-oxetanylmethyl)ether,
triethylene glycol bis(3-ethyl-3-oxetanylmethyl)ether,
tetraethylene glycol bis(3-ethyl-3-oxetanylmethyl)ether,
tricyclodecanediyl dimethylene (3-ethyl-3-oxetanylmethyl)ether,
trimethylolpropane tris(3-ethyl-3-oxetanylmethyl)ether,
1,4-bis(3-ethyl-3-oxetanylmethoxyl)butane,
1,6-bis(3-ethyl-3-oxetanylmethoxy)hexane,
pentaerythritol tris(3-ethyl-3-oxetanylmethyl)ether,
pentaerythritol tetrakis(3-ethyl-3-oxetanylmethyl)ether,
polyethylene glycol bis(3-ethyl-3-oxetanylmethyl)ether,
dipentaerythritol hexatkis(3-ethyl-3-oxetanylmethyl)ether,
dipentaerythritol pentakis(3-ethyl-3-oxetanytmethyl)ether,
dipentaerythritol tetrakis(3-ethyl-3-oxetanylmethyl)ether,
caprolactone-modified dipentaerythritol hexakis(3-ethyl-3-oxetanylmethyl)ether,
caprolactone-modified dipentaerythritol pentakis(3-ethyl-3-oxetanylmethyl)ether,
ditrimethylolpropane tetrakis(3-ethyl-3-oxetanylmethyl) ether,
EO-modified bisphenol A bis(3-ethyl-3-oxetanylmethyl) ether,
PO-modified bisphenol A bis(3-ethyl-3-oxetanylmethyl) ether,
EO-modified hydrogenated bisphenol A bis(3-ethyl-3-oxetanylmethyl)ether,
PO-modified hydrogenated bisphenol A bis(3-ethyl-3-oxetanylmethyl)ether,
EO-modified bisphenol F (3-ethyl-3-oxetanylmethyl)ether, and the like.

"EO" refers to "ethylene oxide", and "PO" refers to "propylene oxide".

Any epoxy-oxetane compound can be used without particular limitation as long as it has air oxirane ring (same as above) and an oxetane ring (same as above) in the molecule, and examples thereof include those described in Patent Literatures 1 to 4. The epoxy-oxetane compounds described in these literatures are hereby incorporated into the present description by reference.

Examples of the acrylic compound include allyl (meth) acrylate, vinyl (meth)acrylate, dicyclopentenyl (meth)acrylate, dicyclopentenyloxyethyl (meth)acrylate, (meth)acrylic acid-modified allyl glycidyl ethers (manufactured by Nagase ChemteX Corporation, "Denacol Acrylate DA111 (trade name)"), urethane (meth)acrylates, epoxy (meth)acrylates, trimethylolpropane tri(meth)acrylate, pentaerythritol tetra (meth)acrylate, ditrimethylolpropane (meth)tetraacrylate, dipentaerythritol hexa(meth)acrylate, butanediol di(meth) acrylate, nonanediol di(meth)acrylate, polypropylene glycol-based (meth)acrylate, bisphenol A di(meth)acrylate tris (2-(meth)acryloyloxyethyl) isocyanurate, (meth)acrylate group-containing polyorganosiloxane, and the like.

In the resin composition of the present invention, as the second curable compound, the above-mentioned polymerizable monomer and polymerizable oligomer may be used in combination; as the polymerizable monomer, the polymerizable monomers exemplified above may be used in combination (different types of polymerizable monomers may be used in combination); and as the polymerizable oligomer, different types of polymerizable oligomer may be used in combination.

As the ratio between the content of the first curable compound and the content of the second curable compound in the resin composition of the present invention, the content of the second curable compound is preferably in an appropriate ratio in the range of from 0 to 1000 times (weight ratio) and more preferably in an appropriate ratio in the range of from 0.01 to 100 times (weight ratio), with respect to the content of the first curable compound.

Examples of a method for curing (polymerizing) the resin composition of the present invention include a photocuring method and a thermally curing method.

Examples of the photocuring method include a method of irradiating an active energy ray and a method of using a photopolymerization initiator in combination therewith. The active energy rays include light, radiation rays, electromagnetic waves, and electron beams, and typically represent light, particularly ultraviolet rays.

As the photopolymerization initiator, a photocationic polymerization initiator can be used, and if necessary, a photoradical polymerization initiator can be used in combination. These initiators may be contained in the resin composition. In photocuring, a heat curing means may be used in combination in order to improve the production efficiency and characteristics of the cured product.

Any photocationic polymerization initiator can be used without particular limitation as long as it is generally used, and examples thereof include onium salts and organometallic complexes.

Examples of the onium salts include diazonium salts, sulfonium salts, and iodonium salts. Examples of the organometallic complexes include iron-allene complexes, titanocene complexes, arylsilanol-aluminum complexes, and the like.

Examples of commercially available industrial chemicals as a photocationic polymerization initiator include "Optomer SP-150 (trade name)" and "Optimer SP-170 (trade name)" manufactured by ADEKA Corporation, "CPI-100P (trade name)" manufactured by San-Apro Ltd., "UVE-1014 (trade name)" manufactured by General Electric Company, "CD-1012 (trade name)" manufactured by Sartomer, and the like.

Examples of the counter anion of the photocationic polymerization initiator include $SbF_6^-$, $AsF_6^-$, $B(C_6F_5)_4^-$, $PF_6^-$, and the like.

The content of the photocationic polymerization initiator in the resin composition of the present invention is preferably in a ratio of from 0.001 to 20 wt %, and more preferably in a ratio of from 0.01 to 10 wt %.

Examples of the photoradical polymerization initiator include:

ketal compounds having a carbon number of 16 to 17 (e.g., acetophenone dimethyl ketal, benzyl dimethyl ketal, etc.);

acetophenone compounds having a carbon number of 8 to 18 (e.g., acetophenone, 2,2-diethoxy-2-phenylacetophenone, 2,2-diethoxy-2-phenylacetophenone, 1,1-dichloroacetophenone, 2-hydroxy-2-methyl-phenylpropan-1-one, diethoxyacetophenone, 1-hydroxycyclohexyl phenyl ketone, 2-methyl-1-[4-(methylthio)phenyl]-2-morpholino-propan-1-one, etc.);

benzophenone compounds having a carbon number of 13 to 21 (e.g., benzophenone, 4-benzoyl-4'-methyldiphenyl sulfide, 4,4'-bismethylaminobenzophenone, etc.);

benzoin compounds having a carbon number of 14 to 18 (e.g., benzoin, benzoin methyl ether, benzoin ethyl ether, benzoin propyl ether, benzoin isobutyl ether, etc.);

anthraquinone compounds having a carbon number of 14 to 19 (e.g., ethylanthraquinone, 2-tert-butylanthraquinone, 2-chloroanthraquinone, 2-amylanthraquinone, etc.):

thioxanthone compounds having a carbon number of 13 to 17 (e.g., 2,4-diethylthioxanthone, 2-isopropylthioxanthone, 2-chlorothioxanthone, etc.);

acylphosphine oxide compounds having a carbon number of 22 to 28 (e.g., 2,4,6-trimethylbenzoyl-diphenyl-phosphine oxide, bis-(2,6-dimethoxybenzoyl)-2,4,4-trimethylpentylphosphine oxide, bis(2,4,6-trimethylbenzoyl)-phenylphosphine oxide, etc.); and the like.

The content of the photoradical polymerization initiator in the resin composition of the present invention is preferably in a ratio of from 0.001 to 20 wt %, and more preferably in a ratio of from 0.01 to 10 wt %.

When photocuring the resin composition of the present invention, a sensitizer such as pyrene, perylene, acridine orange, thioxanthone, 2-chlorothioxanthone, penzoflavin can be used, for example.

On the other hand, in the case Where the resin composition of the invention is thermally cured, a thermal polymerization initiator can be used. As the thermal polymerization initiator, a thermal cationic polymerization initiator can be used, which may be contained in the resin composition.

Any thermal cationic polymerization initiator can be used without particular limitation as long as it is generally used, and examples thereof include various onium salts such as a quaternary ammonium salt, a phosphonium salt and a sulfonium salt, organometallic complexes, and the like.

Examples of onium salts commercially available as industrial chemicals include "Adeka Opton CP-66 (trade name)" and "Adeka Opton CP-77 (trade name)" manufactured by ADEKA Corporation, "San-Aid SI-60L (trade name)", "San-Aid SI-80L (trade name)" and "San-Aid SI-100L (trade name)" manufactured by Sanshin Chemical Industry Co., Ltd., "CI series (trade name)" manufactured by Nippon Soda Co., Ltd., and the like.

Examples of the organometallic complexes include alkoxysilane-aluminum complexes and the like.

The content of the thermal cationic polymerization initiator in the resin composition of the present invention is preferably in a ratio of from 0.001 to 20 wt %, and more preferably in a ratio of from 0.01 to 10 wt %.

As long as the effects of the present invention are not inhibited, the resin composition of the present invention may further contain an additive (modifier) such as:

a pigment (titanium white, cyanine blue, watching red, red iron oxide, carbon black, aniline black, manganese blue, iron black, ultramarine blue, Hansa red, chrome yellow, chrome green, etc.);

an inorganic filler (calcium carbonate, kaolin, clay, talc, mica, barium sulfate, lithopone, gypsum, zinc stearate, perlite, quartz, quartz glass, fused silica, silica powder such as spherical silica, oxides such as spherical alumina, crushed alumina, magnesium oxide, beryllium oxide, and titanium oxide, nitrides such as boron nitride, silicon nitride and aluminum nitride, carbides such as silicon carbide, hydroxides such as aluminum hydroxide and magnesium hydroxide, metals such as copper, silver, iron, aluminum nickel, and titanium, and alloys thereof carbon materials such as diamond and carbon, etc.);

a thermoplastic resin and thermosetting resin (homopolymers such as various high-density, medium-density and low-density polyethylenes, polypropylenes, polybutenes, and polypentenes, ethylene-propylene copolymers, polyamide resins such as nylon-6 and nylon-6,6, vinyl chloride resins, nitrocellulose resins, vinylidene chloride resins, acrylamide resins, styrene resins, vinyl ester resins, polyester resins, phenol resins (phenol compounds), silicone resins, fluorine resins, various elastomer resins such as acrylic rubber and urethane rubber, graft copolymers such as a methyl methacrylate-butadiene-styrene-based graft copolymer and a acrylonitrile-butadiene-styrene-based graft copolymer, etc.);

a reinforcing agent (glass fiber, carbon fiber, etc.);

an anti-sagging agent (hydrogenated castor oil, finely divided anhydrous silica, etc.);

a matting agent (fine silica, paraffin wax, etc.);

an abrasive (zinc stearate, etc.);

an internal release agent (fatty acids such as stearic acid, fatter acid metal salts such as calcium stearate, fatty acid amides such as stearic amide, fatty acid esters, polyolefin wax, paraffin wax, etc.); and a surfactant, a leveling agent, a defoamer, a viscosity adjusting diluent (organic solvent), a coupling agent, a fragrance, and a flame retardant.

In preparing the resin composition of the present invention, the preparation method is not particularly limited, and the resin composition can be prepared by weighing out a predetermined amount of each of the above components and mixing them with stirring. For example, the resin composition of the present invention can be prepared by mixing or melt-kneading the above components by using a roll kneader, a header, an extruder or the like after the preliminary mixing. If necessary, an organic solvent (viscosity adjusting diluent) may be used.

The resin composition of the present invention is polymerized (cured) by irradiation with ultraviolet rays or heating to give a cured product.

Examples of the means for irradiating ultraviolet rays include methods using a light source such as a chemical lamp, a low-pressure mercury lamp, a high-pressure mercury lamp, an ultra-high-pressure mercury lamp, a xenon lamp, and a metal halide lamp.

The irradiation intensity and irradiation time of ultraviolet rays are appropriately set in consideration of a desired irradiation intensity or a desired irradiation time, and also in consideration of the composition and shape (thickness) of the resin composition to be irradiated.

Examples of heating means include methods of hot-air circulation, infrared-heating, and high-frequency-heating. Furthermore, as a curing device, a closed curing furnace, a tunnel furnace capable of continuous curing, and the like can be used.

The heating (curing) temperature and heating (curing) time may be appropriately set in consideration of the composition and shape (thickness) of the resin composition to be irradiated, similar to the case of ultraviolet irradiation.

The resin composition of the present invention is not particularly limited in its use, and can be applied to products (parts/members) in various fields in which the material may be a resin, can be used as a raw material for materials in electric/electronic, optical, architecture, civil engineering, automobile/aircraft, and medical fields, and can be used as a raw material for materials of daily goods and miscellaneous goods.

Examples of parts/members or materials in the electric/electronic fields include copper foils with resin, prepregs, copper-clad laminates, printed wiring boards, solder resist inks, anisotropic conductive films, anisotropic conductive pastes, interlayer insulating materials, adhesives, sealing materials, sealants, insulating materials, heat conductive materials, hot melt materials, paints, potting agents, and the like. Specific examples thereof include:

sealing materials and layer forming materials for printed wiring boards and electronic components, such as an interlayer insulating film and a wiring coating film;

forming materials for display devices, such as a color filter, a polarizing plate, a display material, a resist material, and an alignment film;

forming materials for semiconductor devices, such as a resist material and a buffer coat film; and forming materials for optical components such as a lens, a hologram, an optical waveguide, an optical circuit, an optical circuit component, and an antireflection film.

Further examples include: materials for organic electronics devices such as an organic EL device, an organic transistor and a solar cell; forming materials for rigid wiring boards and flexible printed wiring boards for semiconductor mounting; mounting materials for semiconductor mounting; adhesives for flexible printed wiring boards; sealants for semiconductor; sealants for solar cells; insulating films for semiconductors; coverlay films for flexible printed circuit protection; coating agents for wiring coating; and the like.

Examples of materials in the optical field include core materials for optical fibers, clad materials, wear-resistant coating agents for plastic lenses, and the like.

Examples of materials in the architecture field include:

joint sealing materials, coating materials and primers for exterior materials such as various metal panels and siding boards;

sealing materials, adhesives, injection materials, damping materials, soundproofing materials, conductive materials for electromagnetic wave shielding, and putty material, used between exterior materials, base materials or ceiling materials and interior materials;

adhesive for bonding tiles and stones to exterior wall materials and base materials;

adhesives and pressure-sensitive adhesive agents for bonding wood flooring materials, polymer floor sheets and floor tiles to various floors;

injection materials for crack repair of various exterior materials and interior materials; and the like.

Examples of materials in the civil engineering field include joint sealing materials, coating materials, primers, paints, putty materials, injection materials, spraying materials, and molding materials for various concrete products such as roads, bridges, tunnels, and breakwaters, and the like.

Examples of materials in the automobile/aircraft fields include:

structural materials, adhesives for bodies and parts, sealing materials, coating materials, cushioning materials, damping materials, soundproofing materials, and spraying materials;

adhesives, pressure-sensitive adhesive agents, coating materials, and foam materials for automotive interim;

sealing materials, adhesives and coating materials for steel plate joints; and the like.

Examples of materials in the medical field include artificial bone materials, dental impression materials, medical rubber materials, medical pressure-sensitive adhesive agents, medical device sealing materials, and the like.

EXAMPLES

Hereinafter, the present invention will be described in more detail with reference to Examples and Comparative Examples, but the present invention is not limited thereto. The main raw materials used in Examples and Comparative Examples are as follows.

Main Raw Material 3,3-Bis[(3-cyclohexen-1-ylmethoxy)methyl]oxetane: see Synthesis Example A.
3-Cyclohexene-1-methanol: manufactured by Tokyo Chemical Industry Co., Ltd.
3,3-Bis(bromomethyl)oxetane: manufactured by Tokyo Chemical Industry Co., Ltd.
3,3-Bis[(2-oxiranylmethoxy)methyl]oxetane: see Synthesis Example B, also referred to as epoxy-oxetane compound (2) in some cases.
3,3-Bishydroxymethyloxetane: synthesized in accordance with the method described in "Journal of Polymer Science: Part A Polymer Chemistry, Vol. 27, 3083-3112 (1989)".
Epichlorohydrin: manufactured by Osaka Soda Co., Ltd.
1,3-Bis[(3-ethyloxetane-3-yl)methoxy]-2-propanol: see Synthesis Example C.
3-Ethyl-3-hydroxymethyloxetane: manufactured by Ube Industries, Ltd.
1,3-Bis[(3-ethyloxetane-3-yl)methoxy]-2-(2-oxiranylmethoxy) propane: see Synthesis Example D, also referred to as epoxy-oxetane compound (3) in some cases.

Alicyclic epoxy compound (1): manufactured by Daicel Corporation, "Celloxide 2021P (trade name)", 3',4'-epoxycyclohexyhnethyl 3,4-epoxycyclohexanecarboxylate, see chemical formula (VI-1).

Alicyclic epoxy compound (2): manufactured by Daicel Corporation, "Celloxide 8000 (trade name)", 3,4,3',4'-diepoxybicyclohexyl, see chemical formula (VI-2).

Thermal cationic polymerization initiator (thermal acid generator): manufactured by Sanshin Chemical Industry Co., Ltd., "San-Aid SI-100L (trade name)", dibenzylmethyl-p-hydroxyphenylsulfonium hexafluoroantimonate.

[Chem. 20]

(VI-1)

(VI-2)

Synthesis Example A

Synthesis of 3,3-bis[(3-cyclohexen-1-ylmethoxy)methyl]oxetane

To a 3 L-eggplant flask were charged 295.9 g (2.64 mol) of 3-cyclohexene-1-methanol and 315.9 g of dimethylformamide, followed by ice-cooling to 5° C. while stirring.

Next, thereto was added 285.3 g (2.53 mol) of potassium t-butoxide, and further thereto was added dropwise 258.6 g (1.06 mol) of 3,3-bis(bromomethyl)oxetane, followed by heating to room temperature and stirring for 14 hours.

Next, to the reaction solution was added toluene, followed by washing with water, and the obtained organic layer was concentrated, to thereby obtain 461.6 g of a concentrate. The concentrate was purified by distillation, to thereby obtain 252.5 g (0.82 mol, yield: 78.1%) of the titled olefin-oxetane compound (see Chemical formula (Ia-1)) as a colorless transparent liquid.

$^1$H NMR spectrum data of the olefin-oxetane compound were as follows.

$^1$H-NMR (CDCl$_3$) δ: 5.67 (s, 4H), 4.47 (s, 4H), 3.63 (s, 4H), 3.35 (d, 4H), 2.06 (m, 6H), 1.90 (m, 2H), 1.75 (m, 4H), 1.29 (m, 2H).

[Chem. 21]

(Ia-1)

Synthesis Example B

Synthesis of 3,3-bis[(2-oxiranylmethoxy)methyl]oxetane (epoxy-oxetane Compound (2))

To a 5 L-eggplant flask were charged 391.4 g (3.31 mol) of 3,3-bishydroxymethloxetane, 2438.6 g (26.36 mol) of epichlorohydrin and 12.8 g (0.07 mol) of benzyltrimethylammonium chloride, followed by ice-cooling to 10° C., and thereto was added dropwise 3865.2 g (46.38 mol) of a 48% sodium hydroxide aqueous solution was added dropwise, followed by stirring for 14 hours.

Next, to the reaction solution was added dichloromethane, followed by washing with water, and the organic layer was concentrated. The obtained concentrate was purified by distillation, to thereby obtain 169.1 g (0.73 mol, yield: 22.2%) of the titled epoxy-oxetane compound (see chemical formula (VII)) as a colorless transparent liquid.

$^1$H NMR spectrum data of the liquid were as follows.

$^1$H-NMR (D$_{65}$-DMSO) δ: 4.42 (s, 4H), 3.77 (dd, 2H), 3.63 (d, 4H), 3.31 (dd, 2H), 3.11 (m, 2H), 2.73 (t, 2H), 2.55 (dd, 2H).

[Chem. 22]

(VII)

Synthesis Example C

Synthesis of 1,3-bis[(3-ethyloxetane-3-yl)methoxy]-2-propanol

To a 300 m-eggplant flask were charged 48.79 g (420 mmol) of 3-ethyl-3-hydroxymethyloxetane and 5.76 g (144 mmol) of sodium hydroxide, followed by heating to 4.5° C. while stilling.

Next, thereto was added dropwise 11.10 g (120 mmol) of epichlorohydrin, followed by stirring at 60° C. for 5 hours and then cooling to room temperature.

Next, to the reaction solution were added 600 ml of dichloromethane and 100 ml of water, followed by extraction and washing with water, and the obtained organic layer was concentrated. The obtained concentrate was purified by distillation, to thereby obtain 9.13 g (31.6 mmol, yield: 26.4%) of the titled oxetane compound (see chemical formula (VIIIa)) as a colorless transparent liquid.

$^1$H NMR spectrum data of the oxetane compound were as follows.

$^1$H-NMR (CDCl$_3$) δ: 4.42 (dd, 8H), 3.99 (m, 1H), 3.56 (m, 8H), 2.58 (d, 1H), 1.72 (q, 4H), 0.82 (t, 6H).

[Chem. 23]

(VIIIa)

Synthesis Example D

Synthesis of 1,3-bis[(3-ethyloxetane-3-yl)methoxy]-2-(2-oxiranylmethoxy)propane (epoxy-oxetane Compound (3))

To a 100 ml-eggplant flask were charged 8.00 g (27.74 mmol) of the oxetane compound of which synthesis example is shown in Synthesis Example C, 2.22 g (55.5 mmol) of sodium hydroxide, and 0.51 g (2.77 mmol) of benzyltrimethylammonium chloride, followed by stirring at room temperature.

Next, thereto was added dropwise 7.70 g (83.22 mmol) of epichlorohydrin, followed by stilling for 15 hours.

Next, to the reaction solution were added 50 ml of dichloromethane and 10 ml of water, followed by extraction and washing with water, and the obtained organic layer was concentrated. The obtained concentrate was purified by silica gel column chromatography (hexane/ethyl acetate=1/1 (volume ratio)), to thereby obtain 7.02 g (20.4 mmol, yield: 73.4%) of the titled epoxy-oxetane compound (see chemical formula (VIII)) as a colorless transparent liquid.

$^1$H NMR spectrum data of the liquid were as follows.

$^1$H-NMR (CDCl$_3$) δ: 4.42 (dd, 8H), 3.91 (dd, 1H), 3.74 (m, 1H), 3.58 (m, 9H), 3.13 (m, 1H), 2.78 (t, 1H), 2.62 (dd, 1H), 1.74 (q, 4H), 0.89 (t, 6H).

[Chem. 24]

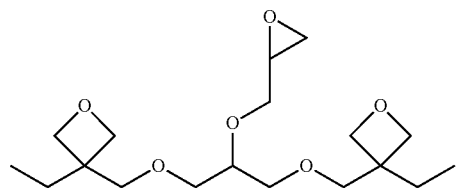

(VIII)

The evaluation tests used in Examples and Comparative Examples are as follows.

Evaluation Test (a) Curability of Resin Composition

Gel time measurement (hot plate method) at 120° C. was performed by using the resin compositions prepared in Examples and Comparative Examples to be described later.

(b) Physical Properties of Cured Product

The resin compositions prepared in Examples and Comparative Examples to be described later were kneaded and defoamed by using a mixing device ("Awatori Rentaro (trade name)"). Then, into a mold frame in which a U-shaped spacer made of 4 mm thick silicone rubber was sandwiched between two release-treated glass plates (120 mm×120 mm×3 mm) and fixed with clips was flowed 15 g of each of the resin compositions. The whole was charged into a blowing oven, then heated at 65° C. for 2 hours and further heated at 150° C. for 2 hours to cure.

Next, after being cooled to room temperature, the cured product was taken out, and a test piece of 10 mm (length)×10 mm (width)×4 mm (thickness) was prepared therefrom by using a cutter.

The glass transition temperature (Tg) and the coefficient of linear expansion (CTE) of these test pieces were measured by using a thermomechanical analyzer (TMA: "TMA7100", manufactured by Hitachi High-Tech Science Corporation) (flow gas: nitrogen gas, temperature-rising condition: 5° C./min.).

Example 1

Synthesis of 3,3-bis[(3,4-epoxycyclohexyl-1-methoxy)methyl]oxetane (Also Referred to as epoxy-oxetane Compound (1) in Some Cases)

To a 300 ml-eggplant flask were charged 5.89 g (19.2 mmol) of 3,3-bis[(3-cyclohexen-1-ylmethoxy)methyl]oxetane, 0.79 g (0.72 g (5.72 mmol) of potassium carbonate, 3.20 g (77.95 mmol) of acetonitrile, and 5.83 g of methanol, followed by stirring under room temperature.

Then, thereto was added dropwise 7.68 g (67.74 mmol) of a 30% hydrogen peroxide aqueous solution, followed by stirring for 18 hours.

Then, to the reaction solution was added 60 g of toluene, and the product was extracted and washed with water. The obtained organic layer was concentrated, and the obtained concentrate was purified by silica gel column chromatography (ethyl acetate/hexane=1/1 (volume ratio)), to thereby obtain 2.89 g (8.54 mmol, yield: 44.5%) of a colorless transparent liquid.

$^1$H NMR spectrum data of the liquid were as follows.

$^1$H-NMR (CDCl$_3$) δ: 4.44 (s, 4H), 3.56 (s, 4H), 3.22 (m, 8H), 2.15 (m, 2H), 2.03 (m, 2H), 1.80 (m, 3H), 1.49 (m, 5H), 1.17 (m, 1H), 1.02 (m, 1H).

The IR spectrum data of this liquid was as shown in the chart shown in FIG. 1.

From these spectrum data, the obtained colorless transparent liquid was identified as the titled epoxy-oxetane compound represented by the chemical formula (I-1).

[Chem. 25]

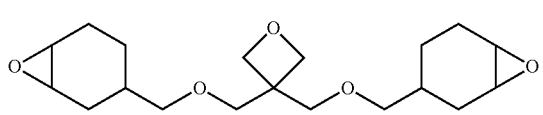

(I-1)

Example 2

A resin composition was prepared by uniformly mixing 100.00 g of the epoxy-oxetane compound (1) of which synthesis example is shown in Example 1 and 0.20 g of a thermal cationic polymerization initiator.

The evaluation tests ((a) Curability of resin composition and (b) Physical properties of cured product) were performed on the resin composition. When the curability of the resin composition and the physical properties of the cured product were evaluated, the test results obtained were as shown in Table 1.

Examples 3 to 5 and Comparative Examples 1 to 13

Resin compositions having the respective compositions shown in Table 1 were prepared in the same manner as in Example 2. When the evaluation tests were performed, the obtained test results were as shown in Table 1.

TABLE 11

| | | Example | | | | Comparative Example | | | | | | | | | | | | |
|---|---|---|---|---|---|---|---|---|---|---|---|---|---|---|---|---|---|---|
| | | 2 | 3 | 4 | 5 | 1 | 2 | 3 | 4 | 5 | 6 | 7 | 8 | 9 | 10 | 11 | 12 | 13 |
| Blending composition (g) | Epoxy-oxetane compound (1) (*1) | 100 | 50 | 25 | 10 | | | | | | | | | | | | | |
| | Epoxy-oxetane compound (2) (*2) | | | | | 100 | 50 | 25 | 10 | | | | | | | | | |
| | Epoxy-oxetane compound (3) (*3) | | | | | | | | | 100 | 50 | 25 | 10 | | | | | |
| | Alicyclic epoxy compound (1) | | 50 | 75 | 90 | | 50 | 75 | 90 | | 50 | 75 | 90 | 100 | | 50 | 25 | 10 |
| | Alicyclic epoxy compound (2) | | | | | | | | | | | | | | 100 | 50 | 75 | 90 |
| | Thermal cationic polymerization initiator | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Evaluation test | Curability: gel time (s) at 120° C. | 11 | 20 | 38 | 53 | 21 | 26 | 35 | 47 | 18 | 23 | 34 | 49 | 80 | 19 | 35 | 46 | 59 |
| | Tg (° C.) | 331 | 233 | 215 | 201 | 323 | 231 | 211 | 190 | 93 | 123 | 139 | 155 | 181 | 360 | 220 | 216 | 188 |
| | CTE ($10^{-8}$/° C.) | 58 | 62 | 65 | 69 | 94 | 90 | 75 | 73 | 114 | 92 | 82 | 77 | 71 | 57 | 62 | 68 | 70 |

(*1)

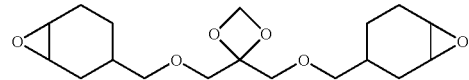

(Example 1)

(*2)

(Synthesis Example B)

(*3)

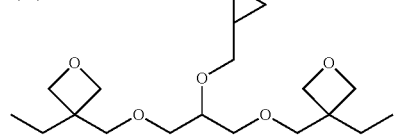

(Synthesis Example D)

Although the present invention has been described in detail by reference to specific embodiments, it will be apparent to those skilled in the art that various modifications and variations are possible without departing from the spirit and scope of the present invention. This application is based on Japanese Patent Application (No. 2017-204824) filed on Oct. 23, 2017 and Japanese Patent Application (No. 2018-175778) filed on Sep. 20, 2018, and the whole contents thereof are incorporated herein by reference.

INDUSTRIAL APPLICABILITY

In the case where the epoxy-oxetane compound of the present invention is used as a raw material of a photo-curable resin and a thermosetting resin, a resin composition exhibiting a crosslinking function and having excellent curability (high curing speed) can be obtained. In addition, the cured product of the resin composition has excellent heat resistance, dimensional stability and brittleness.

Since the resin composition of the present invention can improve various characteristics such as curability, heat resistance, dimensional stability, and brittleness in a well-balanced manner as compared with a conventional resin composition (e.g., containing the alicyclic epoxy compound (1) or (2) as a component), industrial applicability of the present invention is great.

The invention claimed is:

1. An epoxy-oxetane compound represented by the chemical formula (I):

[Chem. 1]

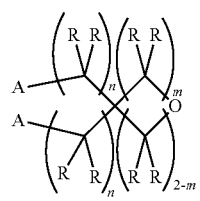
(I)

in the formula (I), A's may be the same as or different from each other, and each independently represents a group represented by the chemical formula (II); R's may be the same as or different from each other, and each independently represents a hydrogen atom or a hydrocarbon group having a carbon number of 1 to 20; m represents an integer of 0 to 2; and n's may be the same as or different from each other, and each independently represents an integer of 0 to 20; and

[Chem. 2]

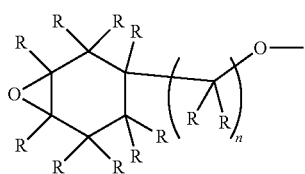
(II)

in the formula (II), R's may be the same as or different from each other, and each independently represents a hydrogen atom or a hydrocarbon group having a carbon number of 1 to 20; and n represents an integer of 0 to 20.

2. A method for synthesizing the epoxy-oxetane compound described in claim 1, comprising: reacting an oxetane compound represented by the chemical formula (III) and an olefin compound represented by the chemical formula (IV) to generate an olefin-oxetane compound represented by the chemical formula (Ia) having a double bond; and then epoxidizing the double bond:

[Chem. 3]

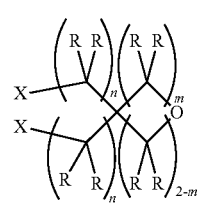
(III)

in the formula (III), R's may be the same as or different from each other, and each independently represents a hydrogen atom or a hydrocarbon group having a carbon number of 1 to 20; m represents an integer of 0 to 2; n's may be the same as or different from each other, and each independently represents an integer of 0 to 20; and X's may be the same as or different from each other, and each independently represents a fluorine atom, a chlorine atom, a bromine atom, an iodine atom, a mesyl group (OMs), a tosyl group (OTs), or a trifluoromethyl group (OTf);

[Chem. 4]

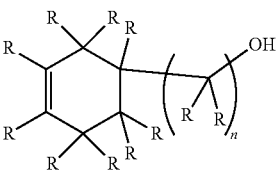
(IV)

in the formula (IV), R's may be the same as or different from each other, and each independently represents a hydrogen atom or a hydrocarbon group having a carbon number of 1 to 20; and n represents an integer of 0 to 20;

[Chem. 5]

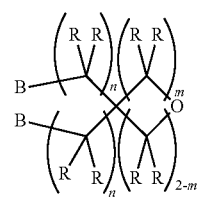
(Ia)

in the formula (Ia), B's may be the same as or different from each other, and each independently represents a group represented by the chemical formula (V); R's may be the same as or different from each other, and each independently represent a hydrogen atom or a hydrocarbon group having a carbon number of 1 to 20; m represents an integer of 0 to 2; and n's may be the same or different from each other, and each independently represents an integer of 0 to 20; and

[Chem. 6]

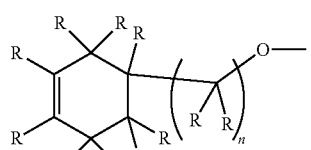
(V)

in the formula (V), R and n have the same meanings as those in the chemical formula (IV).

3. A resin composition comprising the epoxy-oxetane compound described in claim 1.

4. A cured product obtained by curing the resin composition described in claim 3.

* * * * *